United States Patent
Segovia Martinez et al.

(10) Patent No.: US 11,792,578 B2
(45) Date of Patent: Oct. 17, 2023

(54) COCHLEAR STIMULATION SYSTEM WITH AN IMPROVED METHOD FOR DETERMINING A TEMPORAL FINE STRUCTURE PARAMETER

(71) Applicant: Oticon Medical A/S, Smørum (DK)

(72) Inventors: Manuel Segovia Martinez, Vallauris (FR); Julian Skovgaard, Smørum (DK); Pierre Stahl, Vallauris (FR); Kai Dang, Vallauris (FR); Aswin Wijetillake, Smørum (DK)

(73) Assignee: Oticon Medical A/S, Smørum (DK)

( * ) Notice: Subject to any disclaimer, the term of this patent is extended or adjusted under 35 U.S.C. 154(b) by 306 days.

(21) Appl. No.: 16/525,799

(22) Filed: Jul. 30, 2019

(65) Prior Publication Data

US 2020/0045480 A1    Feb. 6, 2020

(30) Foreign Application Priority Data

Jul. 31, 2018  (EP) ..................................... 8186527

(51) Int. Cl.
*H04R 25/00*    (2006.01)

(52) U.S. Cl.
CPC ......... *H04R 25/505* (2013.01); *H04R 25/606* (2013.01)

(58) Field of Classification Search
CPC .................................................. H04R 25/606
See application file for complete search history.

(56) References Cited

U.S. PATENT DOCUMENTS

2009/0304203 A1\* 12/2009 Haykin ................... G10L 21/02
                                                              381/94.1
2013/0218236 A1     8/2013 Churchill

FOREIGN PATENT DOCUMENTS

WO    WO 2017/070138 A1    4/2017

\* cited by examiner

*Primary Examiner* — Rex R Holmes
*Assistant Examiner* — Jennifer L Ghand
(74) *Attorney, Agent, or Firm* — Birch, Stewart, Kolasch & Birch, LLP

(57) ABSTRACT

A cochlear stimulation system for determining a Temporal Fine Structure (TFS) parameter of a spectral component of an incoming acoustic signal is provided. The system comprises a transducer receiving an incoming acoustic signal, and wherein a sampled audio signal of length N samples is provided based on the incoming acoustic signal, a storing unit including a plurality of window frequency differences and/or a plurality of window energy level differences. The system further comprises a signal processor for estimating the TFS parameter of the full frequency range of the sampled audio signal by locating a main spectrum sample of the plurality of spectrum samples having a maximum energy level within a range of frequencies centered around the main spectrum sample, and determining the TFS parameter based on the energy level difference for one or more of the spectrum samples of the group of spectrum samples and the window function.

18 Claims, 14 Drawing Sheets

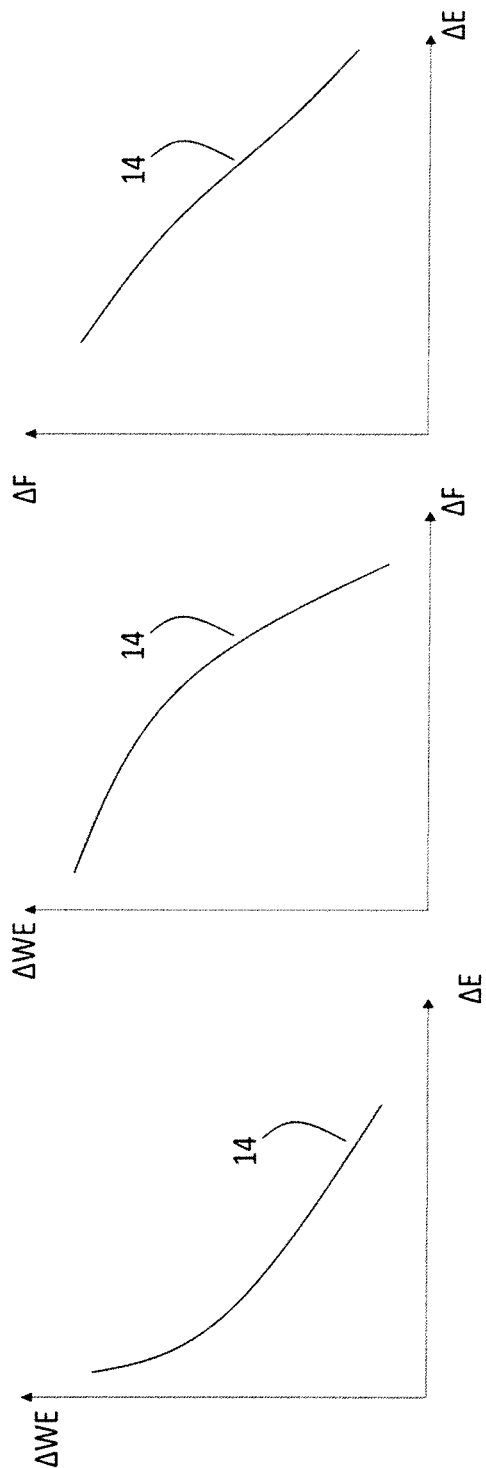

COCHLEAR STIMULATION SYSTEM WITH AN IMPROVED METHOD FOR DETERMINING A TEMPORAL FINE STRUCTURE PARAMETER

TECHNICAL FIELD

The disclosure relates to a cochlear stimulation system for determining a Temporal Fine Structure parameter of a spectral component of a full frequency range of a sampled audio signal.

BACKGROUND

Cochlear implant (CI) are neuroprosthesis that aims to restore hearing sensations in people suffering from severe to profound sensorineural hearing loss. CIs bypass the first auditory chain elements to directly stimulate the Auditory Nerve Fibers (ANF), thus replacing the natural signal processing performed in healthy hears.

Users of conventional cochlear implant (CI) systems can often achieve good speech understanding in quiet conditions, but typically struggle in noisy situations and routinely report poor music enjoyment. These issues are (at least partly) explained by the tendency of clinical CI coding strategies to only encode the slow-varying acoustic temporal envelope (ENV), which is important for speech understanding (in quiet), while discarding the acoustic temporal fine structure (TFS) parameter.

Temporal fine structure (TFS) are changes in the amplitude and frequency of sound perceived by humans over time. These temporal changes are responsible for several aspects of auditory perception, including loudness, pitch and timbre perception and spatial hearing.

Hearing-impaired people have reduced sensitivity to temporal fine structure, and in complex listening situations, hearing-impaired listeners not only suffer from an inability to hear the weak parts of speech signals, they also fail to benefit from TFS. For example, Temporal fine structure in speech signals may be characterized as a sine wave which is equivalently characterized by its frequency F or periodicity T, and key assumptions in the TFS hypothesis are that an accurate decoding of the sine wave in, e.g. a cochlear stimulation system, is based on sensing the periodicity of the sine wave.

The acoustic TFS conveys, in the low frequencies particularly, strong pitch cues that are important for music perception, and interaural timing difference (ITD) cues that help us localize sounds in space. Both TFS-derived pitch and ITD cues are also known to help unimpaired listeners understand speech in noisy conditions. For these reasons, there is keen interest in the CI research community to develop new sound coding strategies that encode TFS parameter, in addition to ENV information.

One of the challenges when developing TFS sound coding strategies is how to reliably extract from the acoustic signal the relevant TFS parameters that is needed to restore the audiological outcome of interest (e.g. pitch perception). Some techniques make assumptions about the underlying nature of the signal itself, which optimizes those techniques to extract TFS information from some types of signals but may result in undesired behavior for other signal types. For example, a technique that assumes the acoustic signal will have a harmonic structure (e.g. vowels in speech) may exhibit undesired behavior when the input signal is (for example) noise-like (e.g. consonants in speech). Other techniques may be sensitive to the presences of undesired components (noise), which may compromise the capability of the strategy to provide coherent feature extraction. Some techniques may have limited frequency resolution, which may restrict the number of TFS parameter that can be detected across-frequency and limit the capability of the of the system to detect and resolve features in the acoustic signal that are too close to one another spectrally.

A commonly employed technique (hereby referred to as the 'filter-band method') to extract TFS parameter for CI coding strategies is to first divide the signal into different frequency bands using a bank of bandpass filters and then extract TFS parameter within each band. This extraction may involve using an amplitude/level threshold-crossing detector that identifies instances when the acoustic signal within the band crosses the predefined threshold: a commonly used threshold detector is a zero-crossing detector that detects all instances when the acoustic signal crosses zero in either the positive or the negative going direction. These threshold crossing are assumed to lock onto threshold-crossings of the main spectral component within the band at a given time, and the timing between threshold crossings are assumed to reflect the frequency of that main spectral component. TFS information extraction could instead involve phase-locked loops (PLL), which are also designed to track the dominant spectral component within the band. With either method, the number of features extracted at a given time is limited by the number of bands, and the resolution of those features will be limited by the spacing of those bands across frequency and their bandwidths. Therefore, if an acoustic signal comprises M key spectral components and the system operates on N bands, where M>N, the system will only be able to extract information from N spectral components and will discard the remaining M-N. For this case, there will be one more bands within which multiple acoustic signal components fall. As a result, the system will not be able to resolve and extract the individual spectral components within those bands, and the single extracted feature for each of those bands will comprise a mixture of information from all components within the band. The frequency resolution of such a system can be increased by increasing the number of filters within the filter-bank, but will come at the cost of increased computational complexity and system latency. Another drawback of the filterbank method is that the individual filters themselves will have limited spectral selectivity, which causes unwanted spectral components to leak into each band from adjacent bands, and can again cause undesired mixing of information from multiple audio signal components. The spectral selectivity of these filters can be improved by increasing the number of filter-coefficients, which again will introduce increased computational complexity and system latency.

SUMMARY

An aspect of the present disclosure is to provide a cochlear stimulation system aiming for overcoming the mentioned disadvantages with the above described known solution, e.g. the filter-band method.

An aspect of the present disclosure is to provide a cochlear stimulation system that avoids dividing an incoming acoustic signal into frequency bands using filterbank and extracting a TFS parameter within those bands, i.e. the extraction of TFS parameter is extracted from the full frequency bandwidth of the incoming acoustic signal.

The aspect of the present disclosure is achieved by a cochlear stimulation system for determining a Temporal Fine Structure (TFS) parameter of a spectral component of an incoming acoustic signal. The system comprising; a transducer configured for receiving the incoming acoustic signal, and wherein a sampled audio signal of length N samples is provided based on the incoming acoustic signal, a storing unit including a plurality of window frequency differences and/or a plurality of window energy level differences generated from a window spectrum of a window function of length N, a window analyzer for providing a plurality of spectrum samples by performing a time to frequency transformation and a multiplication of the sampled audio signal with the window function in a time domain, or a convolution of the window spectrum in frequency domain and the sampled audio signal in frequency domain. The system further comprises a signal processor for estimating the Temporal Fine Structure parameter of the full frequency range of the sampled audio signal, and wherein the Temporal Fine Structure parameter is estimated by locating a main spectrum sample of the plurality of spectrum samples having a maximum energy level, estimating for a group of spectrum samples of the plurality of spectrum samples an energy level difference for one or more of the spectrum samples of the group of spectrum samples, within a range of frequencies centered around the main spectrum sample, and determining the Temporal Fine Structure parameter based on the energy level difference for one or more of the spectrum samples of the group of spectrum samples and the window function.

The aspect of the present disclosure is achieved by a cochlear stimulation system for determining a Temporal Fine Structure (TFS) parameter of a spectral component of an incoming acoustic signal. The system comprising; a transducer configured for receiving the incoming acoustic signal, and wherein a sampled audio signal of length N samples is provided based on the incoming acoustic signal, a storing unit including a plurality of window frequency differences and/or a plurality of window energy level differences generated from a window spectrum of a window function of length N, a window analyzer for providing a plurality of spectrum samples by performing a time-to-frequency transformation and a multiplication of the sampled audio signal with the window function in a time domain, or a convolution of the window spectrum in frequency domain and the sampled audio signal in frequency domain. The system further comprises a signal processor for estimating the Temporal Fine Structure parameter of the full frequency range of the sampled audio signal, and wherein the Temporal Fine Structure parameter is estimated by locating a main spectrum sample of the plurality of spectrum samples having a maximum energy level, estimating for a group of spectrum samples of the plurality of spectrum samples an energy level difference for one or more of the spectrum samples of the group of spectrum samples, within a range of frequencies centered around the main spectrum sample, estimating a frequency difference for one or more of the energy level differences of the group of spectrum samples based on the plurality of window frequency differences and the plurality of window energy level differences, and determining the Temporal Fine Structure parameter based on the frequency difference for one or more of the energy level difference of the group of spectrum samples and the window function, or the energy level difference for one or more of the spectrum samples of the group of spectrum samples and the window function.

Providing TFS parameters to patients can potentially help improve listening outcomes in complex environments. The full frequency bandwidth solution provides a more accurate way to extract important TFS parameter (e.g. fundamental frequencies and harmonics) from the incoming acoustic signal. The more accurate way of extracting TFS parameter, i.e. a better spatial and temporal resolution of the TFS parameter is provided by having the full frequency bandwidth solution.

Furthermore, the present disclosure has a further advantage which is a better trade-off between accuracy versus computational complexity and system latency. For example, an FFT size of 256 may be used, and which would provide essentially 128 bands that have frequency selectivity based on the window function used. Instead, using a filter bank with 128 filters may produce a similar or better accuracy then the present disclosure, but it would use an enormous computational power.

The full frequency range of the sampled audio signal may be between 20 Hz and 20.000 Hz.

Window energy level differences may be prestored in the storing unit, and the window energy level differences may be theorical values which are fitted to a window function. For each of the window energy level difference a window frequency difference is retrieved from the fitting to the window function.

Based on an input of energy level differences of the group of spectrum samples, the storing unit may be configured to retrieve window energy level differences and/or the corresponding window frequency differences by correlating the energy level differences with the window energy level differences, and those window energy level differences which correlates best are retrieved and transmitted to the signal processor. The corresponding window frequency differences may also be transmitted to the signal processor. In another example, the window frequency difference may be retrieved and transmitted to the signal processor without the window frequency differences.

TFS parameter is important to be encoded. For music, fundamental frequencies and harmonics are key for pitch perception, which the present disclosure is able to estimate more accurately than other methods (e.g. filter banks) and with a better trade-off between accuracy and computational power. The TFS parameter may be assigned to electrodes by later processing blocks without restrictions. Therefore, if the present disclosure detects, for example a set of fundamental frequencies and harmonics, a later block in the signal processor could make decisions on how to distribute those harmonics to different electrodes to optimize pitch perception. The distribution is done by the signal processor, but how this is done within the signal processor is not described in this disclosure as this is not essential for the invention and is considered to be common knowledge for the skilled person in the art.

The present disclosure provides a simpler and less demanding computational signal processing for extraction of TFS parameter because the use of a filter bank is avoided. Furthermore, if a solution including a filter bank needs to provide a similar resolution as the present disclosure, the filter bank needs many more filter coefficients, and which results in a more computationally demanding solution.

Based on the Temporal Fine Structure parameters, events may be generated and which ultimately become pulses sent to different electrodes.

An event generator may be configured to provide an event for providing the Temporal Fine Structure parameter to an electrode of a plurality of electrodes, wherein the event may be generated based on The Temporal Fine Structure parameter, such as a phase parameter.

Alternatively, the event may be generated when a phase difference between a constant phase factor, being between 0 and 2*pi, and the phase parameter is equal to zero or a predetermined constant. The phase difference may be divided by a sample frequency of a frame clock event for determining the Temporal Fine Structure parameter.

The event may be generated after a time delay ($\Delta t$), wherein the time delay may be determined by following equation;

$$t = \frac{2\pi - \varphi_{TFS}}{\Delta \varphi}, ,$$

where $\Delta\varphi$ is a ratio between a frame clock event for determining the Temporal Fine Structure parameter (TFS) and the frequency parameter, and $\varphi_{TFS}$ is the phase parameter.

The frame clock determines the rate for determine the temporal fine structure for each of the sampled audio signal of length N.

A cochlear implant may comprise the cochlear stimulation system as disclosed above, wherein the cochlear implant may comprise an array of electrodes configured to stimulate auditory nerves of the user based on the Temporal Fine Structure parameter(s).

The cochlear stimulation system may comprise a behind-the-ear (BTE) unit, an inductor unit and an implant. The BTE unit may be connected to the inductor unit wirelessly or wired, and the inductor unit may be inductively connected to the implant through the skin of the user. The transducer, such as a microphone or a mems microphone may be part of the BTE unit or the inductor unit. The cochlear stimulation system may include one or more transducers, such as 1, 23, or 4 transducers. The transducer may include an analog-to-digital converter or the transducer may be connected to the analog-to-digital converter configured to provide the sampled audio signal.

The incoming acoustic signal may be divided into multiple sample frames of length N samples, i.e. a sampled audio signal of length N samples, and wherein the cochlear stimulation system may be configured to determine the Temporal Fine Structure parameter for each of the samples frames, i.e. the sampled audio signal of length N samples.

The cochlear stimulation system may be configured to determine multiple temporal Fine Structure parameters sequentially or in parallel for each sampled audio signal of length N samples.

Furthermore, the cochlear stimulation system may be configured to determine the temporal Fine structure parameter for multiple sampled audio signals of length N samples.

The sampled audio signal may include N number of samples, wherein N denotes the samples size of the audio signal. N number will affect the spectral resolution, i.e. the larger the N is the better the resolution becomes. However, a high N number of samples demands more computational power of the signal processor. A reasonable N number of samples may be a tradeoff between computational power and temporal resolution of the TFS parameter.

The storing unit may be part of the BTE unit or an external unit, such as a server, mobile device, cloud server or any devices which is configured to be connected wirelessly to the cochlear stimulation system, e.g. the BTE unit, inductor unit configured to be arranged on the skull of the user.

The storing mean may include the plurality of window frequency differences and the plurality of window energy level differences generated from a window spectrum of a window function of length N. In general, a window function (also known as an apodization function or tapering function) is a mathematical function that is zero-valued outside of a chosen interval of length N. For instance, a function that is constant inside the interval of length N and zero elsewhere is called a rectangular window. When another function or waveform/data-sequence, such as a time-to-frequency transformed sampled audio signal is convolved with a window function in frequency domain or a sampled audio signal is multiplied with a window function in time domain and then transformed into frequency domain, the product is also zero-valued outside the interval. Examples of other window functions could be a Hann window, a Hamming window, a Tukey window, a Blackmann window, a flat top window and etc.

The window spectrum includes a sinusoidal signal which represents an ideal shaped sinusoidal signal of the sampled audio signal. The window spectrum may be determined based on a theoretical sinusoidal model and the sampled audio signal, or based on the theoretical sinusoidal model alone.

The plurality of spectrum samples defines a length of the time to frequency transformation, and the time to frequency transformation may be based on Fast Fourier Transformation.

Each of the window energy level difference of the plurality of window energy level differences may be between a first energy level of a first sample at a first frequency of the window spectrum and a second energy level at a second frequency of a second sample, wherein the first frequency and the second frequency are within the range of frequencies centered around the main spectrum sample, or the window energy level difference of the plurality of window energy level difference may be between a first energy level of the first sample and the energy level at the frequency parameter, wherein the first frequency is within the range of frequencies centered around the main spectrum sample.

The storing mean may comprise the plurality of window frequency differences and the plurality of window energy level differences between a first energy level of a first sample at a first frequency of the window spectrum and a second energy level at a second frequency of a second sample, wherein the first frequency and the second frequency are within the range of frequencies centered around the main spectrum sample, and another plurality of window energy level differences between a first energy level of the first sample and the energy level at the frequency parameter, wherein the first frequency is within the range of frequencies centered around the main spectrum sample.

The storing unit may comprise one or more window functions, e.g. a window function including energy as a function of frequency, peak energy difference as a function of frequency, and peak energy difference as a function of energy difference of a first sample and a second sample. For example, within the interval of length N, the window function includes a function between the energy per sample as a function of frequency, or peak energy difference between samples as a function of frequency, and/or peak energy difference as a function of energy difference of a first spectrum sample and a second spectrum sample.

Peak energy difference of a sample or a spectrum sample may be determined by calculating the difference between a first energy of the sample or the spectrum sample and a second energy of another sample or spectrum sample where both samples or spectrum samples have a frequency within the range of frequencies.

The window analyzer provides the plurality of spectrum samples, wherein each of the spectrum sample is band limited to a frequency. The window analyzer provides the plurality of spectrum samples by performing the time-to-frequency transformation, such as Fast Fourier Transformation, of the sampled audio signal and the window function and the multiplication of the sampled audio signal with the window function or the convolution of the sampled audio signal with the window spectrum/window function. In one example, the sampled audio signal may be multiplied with the window function, and the multiplied sampled audio signal may then be transformed from time to frequency, or, both the sampled audio signal and the window function may be transformed from time-to-frequency after or before performing the multiplication with each other or the convolution with each other, respectively.

The number of samples, i.e. N samples, for both the window function and the sampled audio signal are the same.

The time-to-frequency transformation of the window function may be performed only once when providing the plurality of spectrum samples.

The window analyzer may be configured to perform a convolution of the window spectrum in frequency domain and the sampled audio signal in frequency domain.

The window analyzer may be part of the BTE unit or the inductor unit. The window analyzer may be connected to the storing unit and the transducer.

The signal processor is configured to estimate the TFS parameter over the full frequency range of the sampled audio signal. The signal processor may locate the main spectrum sample of the plurality of spectrum samples which has the highest energy of all spectrum samples of the plurality of spectrum samples. From the main spectrum sample, the actual center frequency of the actual spectral component in the audio signal that produced the main spectrum sample is to be determined and is assigned as a Temporal Fine Structure parameter, e.g. a frequency parameter.

The main spectrum sample is used for selecting one or more spectrum samples defining a group of spectrum samples, and where a frequency of each of the spectrum samples of the group of spectrum samples is within a range of frequencies that is around the frequency of the main spectrum sample. For each of the spectrum sample of the group of spectrum samples, the energy level difference is estimated. The range may be between +/−50 Hz and +/−100 Hz, +/−50 Hz and +/−200 Hz, +/−50 Hz and +/−300 Hz, +/−50 Hz and +/−400 Hz, +/−100 Hz and +/−400 Hz, or +/−200 Hz and +/−600 Hz. For example, if the frequency of the main spectrum sample is 4100 Hz, the range may be between 3900 HZ and 4400 Hz.

The energy level difference, i.e. sample energy level difference, for one or more of the spectrum samples of the group of spectrum samples may be between a first energy level of a first spectrum sample of the group of spectrum samples and a second energy level of a second spectrum sample of the group of spectrum samples. For example, the first spectrum sample and the second spectrum sample may be two neighboring samples in frequency or located anywhere within the range of frequencies around the frequency of the main spectrum sample. Another example, the first spectrum sample may be any spectrum samples of the group of spectrum samples located within the range of frequencies around the frequency of the main spectrum sample, and the second spectrum sample may be the main spectrum sample.

The frequency difference for one or more of the energy level differences of the group of spectrum samples may be estimated based on the plurality of window frequency differences and the plurality of window energy level differences. The estimation of each frequency difference may for example be provided by interpolation of the plurality of window frequency differences and the plurality of window energy level differences at each energy level differences. Each window energy level difference is unique, i.e. the window energy differences are not the same. Thereby, the estimated frequency difference for the estimated energy level difference is unique, i.e. only one frequency difference is valid for the estimated energy level difference.

The frequency differences may be determined by interpolating the frequency differences from the plurality of window frequency differences and the plurality of window energy level differences based on the energy level differences between the spectrum samples of the group of spectrum samples, i.e. the window function may comprise a relation between the plurality of window frequency differences and the plurality of window energy level differences and the input to the window function is the energy level differences and the output of the window function is the frequency differences. The frequency differences may be determined by other methods than interpolation.

The Temporal Fine Structure parameter may be determined based on the energy level difference for one or more of the spectrum samples of the group of spectrum samples. The signal processor may be configured to determine an energy difference, hereby referred to as the peak energy difference between the true energy of the signal component and one or more spectrum samples of the group of spectrum samples based on the window function and the energy difference of one or more of the spectrum samples of the group of spectrum samples.

The window function may include peak energy difference as a function of energy difference between samples. Each peak energy difference of the group of spectrum samples may be determined by interpolation of the window function at each energy difference. The true energy of the audio signal component, i.e. the energy parameter, may then be estimated by appropriately combining one or more peak energy differences with the energies of one or more spectrum samples The combination of the peak energy differences may include averaging of the peak energy differences into the energy parameter.

The energy parameter denotes the energy of the actual spectral component of interest in the audio signal.

The Temporal Fine Structure parameter may comprise the energy parameter of the component of the audio sample, and wherein the energy parameter may be determined by;
  extraction of the window energy level difference of one or more spectrum samples of the group of spectrum samples based on the window function and the energy difference of one or more of the spectrum samples of the group of spectrum samples, or based on the window function (different than the previous window function) and the frequency difference for one or more of the spectrum samples of the group of spectrum samples,
  determine the energy parameter based on the window energy level difference of one or more spectrum samples of the group of spectrum samples and an energy level of one or more of the spectrum samples of the group of spectrum samples.

A peak energy may be determined for each of spectrum samples of the group of spectrum samples by summing the energy level of a spectrum sample of the group of spectrum sample with the window energy level difference of the spectrum sample of the group of spectrum sample, and the energy parameter may be determined appropriately combining one or more peak energies (i.e. computing the average, weighted averaged, median etc.).

The advantage of using window function and interpolation and/or averaging compared to known solution including filter bank(s) is that the energy of the sampled audio signal of length N is determined more precise if considering the computational power to be equal for both methods, e.g. the filter bank method and the present disclosure. Furthermore, the way the energy parameter is determined is less insensitive to evolvement of, e.g. the pitch, from frequency band to frequency band.

For determine a more precise energy parameter, the signal processor may be configured to determine an energy compensation factor including an energy difference between an energy level of a maximum energy level of a main lobe of a rectangular window spectrum and an energy level of the maximum energy level of the window function, and wherein the energy parameter is determined by combining the energy compensation factor with the peak energies of one or more spectrum samples from the group of spectrum samples An example of determine the energy compensation factor, Ec, may be expressed as: $E_C = E_{rec} + E_{win}$, where $E_{rec}$ is the maximum energy level of the rectangular window spectrum, and Ewer is the maximum energy level of the window function.

A further advantage with energy compensation factor is that the energy parameter is insensitive to which window function is selected by the signal processor or stored in the storing unit. Thereby, the present disclosure becomes more robust.

The plurality of spectrum samples, determined by the window analyzer, includes both the phase and the energy of each spectrum samples.

The Temporal Fine Structure parameter may comprise a phase parameter determined at the frequency parameter of the spectral component by interpolation of phases of the spectrum samples of the group of spectrum samples.

A quality marker may be determined by a variance/difference/error/spread of each of the estimated spectral component center frequency or the estimated spectral component energy level derived from one or more of the spectrum samples of the group of spectrum samples from the frequency parameter or from the energy parameter, respectively.

The quality marker may be a descriptor for how reliable the estimate of the Temporal Fine Structure parameter is. It will also indicate how sinusoidal the spectral component may be. A maximum valued quality marker implies a sinusoidal spectral component (i.e. a bandwidth approaching zero), and a minimum valued quality marker implies that the spectral component is broadband.

The quality marker may be used for determine whether or not to accept the Temporal Fine Structure parameter. For example, if the quality marker is low, the Temporal Fine Structure parameter could be discard and a previously determined Temporal Fine Structure parameter having an acceptable quality marker may instead be used, or an averaged Temporal Fine Structure parameter of a number of previous determined Temporal Fine Structure having an acceptable quality marker may instead be used.

The group of spectrum samples may comprise two or more spectrum samples, or a number of spectrum samples such that a precise Temporal Fine Structure parameter can be determined.

The window analyzer may be configured to determine another plurality of spectrum samples by applying a frequency shift to the sampled audio signal and performing a time-to-frequency transformation and a multiplication of the frequency shifted sampled audio signal with the window function in the time domain, or a convolution of the window spectrum and the frequency shifted sampled audio signal in frequency domain, and applying the another plurality of spectrum samples into the plurality of spectrum samples.

The application of the another plurality of spectrum samples into the plurality of spectrum samples may be provided by combining, summing, interleaving or merging.

The window analyzer may be configured to determine the another plurality of spectrum samples and the plurality of spectrum samples without the frequency shift sequentially or in parallel. In parallel, the processing time of providing the plurality of spectrum samples including the another plurality of spectrum samples which is frequency shifted is minimal increased if having multiple processor cores.

The temporal Fine Structure parameter may be determined based on a frequency difference for one or more of the energy level differences of the group of spectrum samples. The frequency difference may be estimated for each of the energy level difference of the group of spectrum samples based on the plurality of window frequency differences and the plurality of window energy level differences. The Temporal Fine Structure parameter may comprise a frequency parameter of the spectral component, i.e. the actual center frequency of the spectral component, wherein the frequency parameter is determined by;

estimating a center frequency for one or more of the frequency difference of the group of spectrum samples based on a frequency of one or more of the spectrum samples of the group of spectrum samples and the frequency difference of one or more of the spectrum samples of the group of spectrum samples, and computing the frequency parameter based on the center frequencies derived from one or more of spectrum samples of the group of spectrum samples.

The advantage of the way the signal processor determines the frequency parameter compared to known solution including filter bank(s) is that the center frequency of the spectral component is determined with greater precision and with less interference from content from other frequency bands with lower computational cost.

By applying the another plurality of spectrum samples into the plurality of spectrum samples results in interpolation that yields narrower spacing between spectral sampling points, i.e. more spectrum samples may be included in the group of spectrum samples within the range of frequencies centered around the frequency of the main spectrum sample. This can improve the precision of the Temporal Fine Structure parameter.

The Temporal Fine Structure parameter may comprise the frequency parameter, the energy parameter and the phase parameter of the incoming acoustic signal. As mentioned before, the incoming acoustic signal may be represented by a sine wave which is characterized by its frequency parameter, energy parameter, (e.g. the height of the sine wave), and phase parameter.

The frequency parameter may be

In the present disclosure the energy of the samples, energy difference or window energy difference may also be denoted as power, power difference or window power difference or amplitude, amplitude difference or window amplitude difference. It is not essential whether it is power, energy or amplitude which is used in order to determine the Temporal Fine Structure parameter.

A cochlear implant may comprise the cochlear stimulation system.

A hearing aid may comprise the cochlear stimulation system and/or the cochlear implant.

Definitions

In the present context, the cochlear stimulation system or a hearing aid including the cochlear stimulation system refers to a device, which is adapted to improve and/or augment hearing capability of a user by receiving acoustic signals from the user's surroundings, generating corresponding electric audio signals, possibly modifying the electric audio signals and providing the possibly modified electric audio signals as audible signals to at least one of the user's ears via stimulation provided by an array of electrodes.

More generally, a hearing aid comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit (e.g. a signal processor, e.g. comprising a configurable (programmable) processor, e.g. a digital signal processor) for processing the input audio signal and an output unit for providing an audible signal to the user in dependence on the processed audio signal. The signal processor may be adapted to process the input signal in the time domain or in a number of frequency bands. In some hearing aids, an amplifier and/or compressor may constitute the signal processing circuit. The signal processing circuit typically comprises one or more (integrated or separate) memory elements for executing programs and/or for storing parameters used (or potentially used) in the processing and/or for storing information relevant for the function of the hearing aid and/or for storing information (e.g. processed information, e.g. provided by the signal processing circuit), e.g. for use in connection with an interface to a user and/or an interface to a programming device. In some hearing aids, the output unit may comprise transducer, such as e.g. a vibrator for providing a structure-borne or liquid-borne acoustic signal. In some hearing aids, the output unit may comprise one or more output electrodes for providing electric signals (e.g. a multi-electrode array for electrically stimulating the cochlear nerve).

In some hearing aids, the vibrator may be adapted to provide a structure-borne acoustic signal transcutaneously or percutaneously to the skull bone. In some hearing aids, the vibrator may be implanted in the middle ear and/or in the inner ear. In some hearing aids, the vibrator may be adapted to provide a structure-borne acoustic signal to a middle-ear bone and/or to the cochlea. In some hearing aids, the vibrator may be adapted to provide a liquid-borne acoustic signal to the cochlear liquid, e.g. through the oval window. In some hearing aids, the output electrodes may be implanted in the cochlea or on the inside of the skull bone and may be adapted to provide the electric signals to the hair cells of the cochlea, to one or more hearing nerves, to the auditory brainstem, to the auditory midbrain, to the auditory cortex and/or to other parts of the cerebral cortex.

A 'hearing system' refers to a system comprising one or two hearing aids, e.g. one BTE unit and a cochlear implant, and a 'binaural hearing aid system' refers to a system comprising two hearing aids and being adapted to cooperatively provide audible signals to both of the user's ears. Hearing aid systems or binaural hearing aid systems may further comprise one or more 'auxiliary devices', which communicate with the hearing aid(s) and affect and/or benefit from the function of the hearing aid(s). Auxiliary devices may be e.g. remote controls, audio gateway devices, mobile phones (e.g. SmartPhones), or music players. Hearing aid, hearing aids systems or binaural hearing aid systems may e.g. be used for compensating for a hearing-impaired person's loss of hearing capability and/or augmenting a normal-hearing person's hearing capability and/or conveying electronic audio signals to a person. Hearing aids or hearing aid systems may e.g. form part of or interact with public-address systems, active ear protection systems, handsfree telephone systems, car audio systems, entertainment (e.g. karaoke) systems, teleconferencing systems, classroom amplification systems, etc.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIGS. 7A, 7B and 7C illustrate an example of a window function.

DETAILED DESCRIPTION

Figure 1:
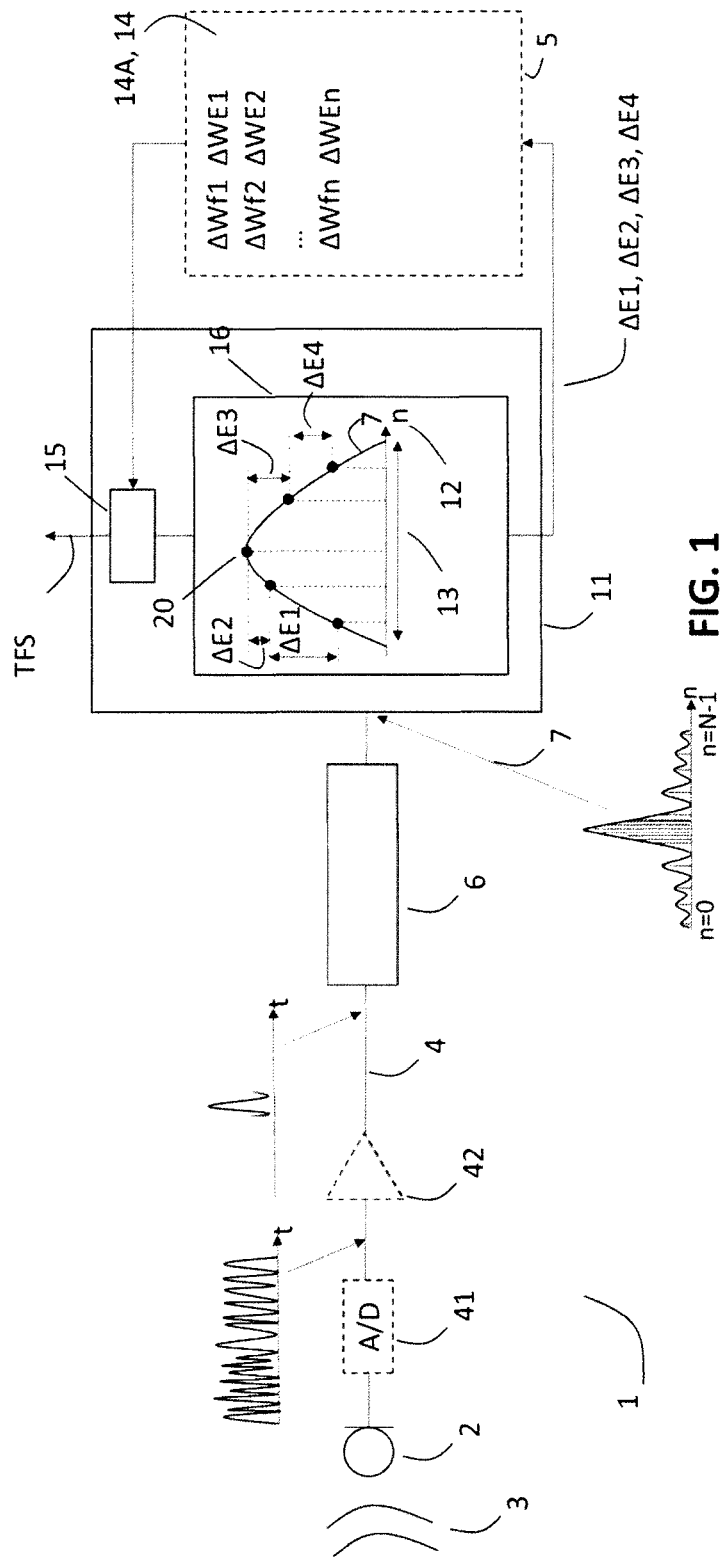
FIG. 1, illustrates an example of a cochlear stimulation system.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

It is intended that the structural features of the devices described above, either in the detailed description and/or in the claims, may be combined with steps of the method for determining Temporal Fine Structure parameter, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

FIG. 1 illustrates an example of a cochlear stimulation system 1 for determining a Temporal Fine Structure (TFS) parameter of a spectral component of an incoming acoustic signal (3). The system 1 comprises a transducer 2 configured for receiving the incoming acoustic signal 3, and wherein a sampled audio signal 4 of length N samples is provided based on the incoming acoustic signal (3).

The system 1 is configured to determine TFS parameter for multiple sampled audio signals 4 of length N samples either sequentially or in parallel in dependence of a frame clock event.

The system 1 comprises a storing unit 5 which includes a plurality of window frequency differences ΔWF and/or a plurality of window energy level differences ΔWE generated from a window spectrum 14A of a window function 14 of length N.

The transducer 2 is connected to a window analyzer 6, by an analog-to-digital converter which is configured to generate the sampled audio signal 4 of length N samples and which is forwarded to the window analyzer 6.

Optionally, the transducer 2 is connected to an analog-to-digital converter generating multiple samples, including the sampled audio signal 4 of length N samples, based on the incoming acoustic signal 3. The multiple samples are stored in a sample buffer, and the sample buffer may then transmit the sampled audio signal 4 to the window analyzer 6. The sample buffer is not shown in FIG. 1.

The window analyzer 6 is connected to the storing unit 5.

The window analyzer 6 is configured for providing a plurality of spectrum samples 7 by performing a time to frequency transformation 8 (not shown) and a multiplication 9 (not shown) of the sampled audio signal with the window function 14 in a time domain, or a convolution 10 (not shown) of the window spectrum 14A in frequency domain and the sampled audio signal (4) in frequency domain.

The plurality of spectrum samples 7 is forwarded to a signal processor 11 which is configured for estimating the Temporal Fine Structure parameter (TFS) of the full frequency range of the sampled audio signal 4.

The Temporal Fine Structure parameter (TFS) is estimated by; locating 16 a main spectrum sample 20 of the plurality of spectrum samples 7 having a maximum energy level. The main spectrum sample 20 having the maximum energy level indicates a sample which is positioned in vicinity to an actual center frequency of a main lobe of the spectrum samples 7. The actual center frequency is a TFS parameter denoted as a frequency parameter $F_{TFS}$.

For a group of spectrum samples 12 of the plurality of spectrum samples 7, an energy level difference ΔE for one or more of the spectrum samples of the group of spectrum samples 12 is estimated, within a range of frequencies 13 centered around the main spectrum sample 20.

In the present example, the group of spectrum samples 12 includes five spectrum samples, which includes the main spectrum sample 20 and four other spectrum samples. Each of the samples is defined by an energy level and a frequency. For each of the spectrum samples within the group of spectrum samples 12 the energy level difference ΔE is determined between two neighboring samples in frequency.

The signal processor 11 is then configured to extract the relevant window function for which TFS parameter is to be determined. The extraction of the relevant window function is done by selecting the window function which corresponds best to the sampled audio signal, e.g. by determining standard deviation between each of the window function and the sampled audio signal and then select the window function which has the lowest standard deviation. The selected window function is the relevant window function. In this present example, the energy level differences (ΔE1, ΔE2, ΔE3, ΔE4) are used for extracting the relevant window function 14 from the storing unit 5.

The Temporal Fine Structure parameter (TFS) is then determined 15 based on the energy level differences (ΔE1, ΔE2, ΔE3, ΔE4) and the window function 14 extracted based on the energy level differences. This approach is also described in FIG. 4B.

Figure 2:
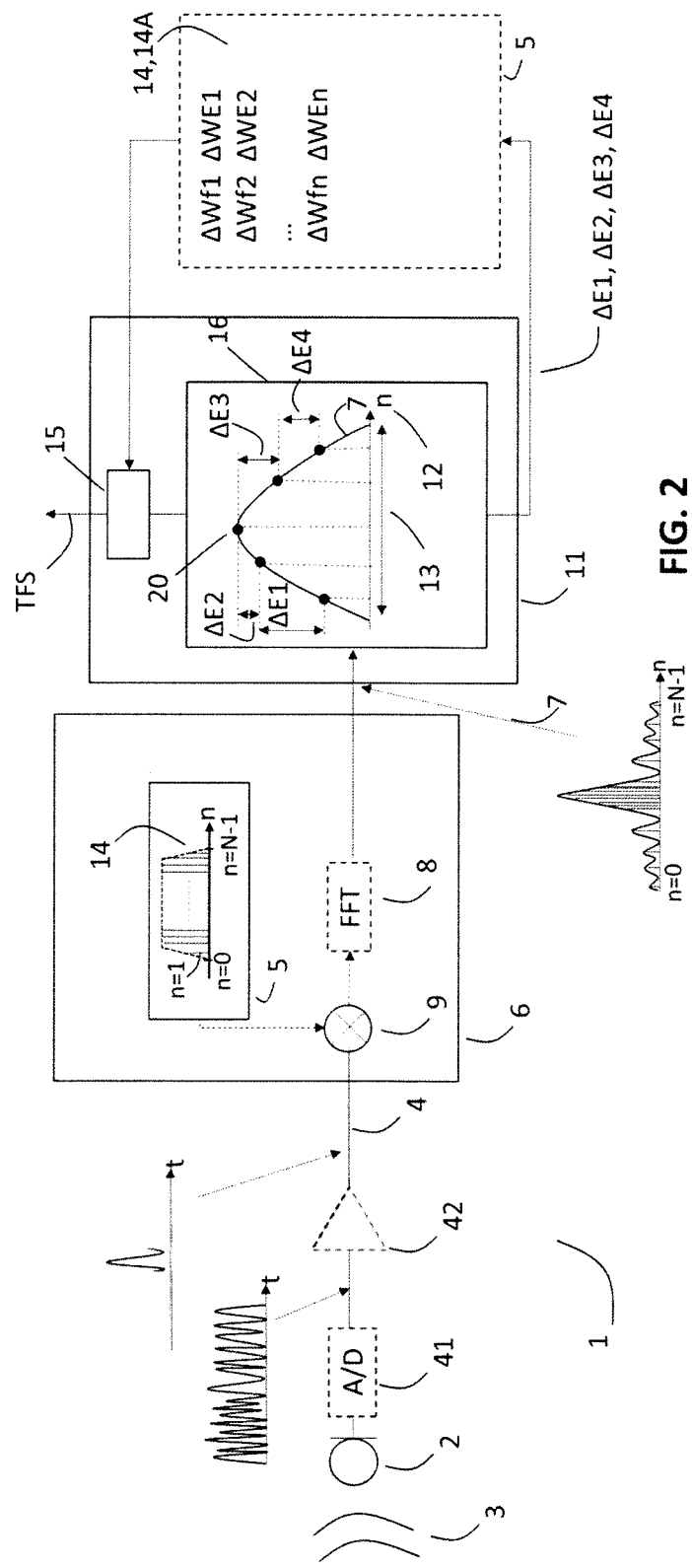
FIG. 2, illustrates a further example of the cochlear stimulation system.

FIG. 2 illustrates a further example of the cochlear stimulation system 1 where the window analyzer is configured to perform a time-to-frequency transformation, e.g. a Fast Fourier Transformation, of the multiplication 9 of the sampled audio signal 4 with the window function 14. The window analyzer 6 may receive the window function 14 from the storing unit 5, e.g. by a request signal transmitted to the storing unit.

The plurality of spectrum samples 7 is then transmitted to the signal processor 11.

Figure 3:
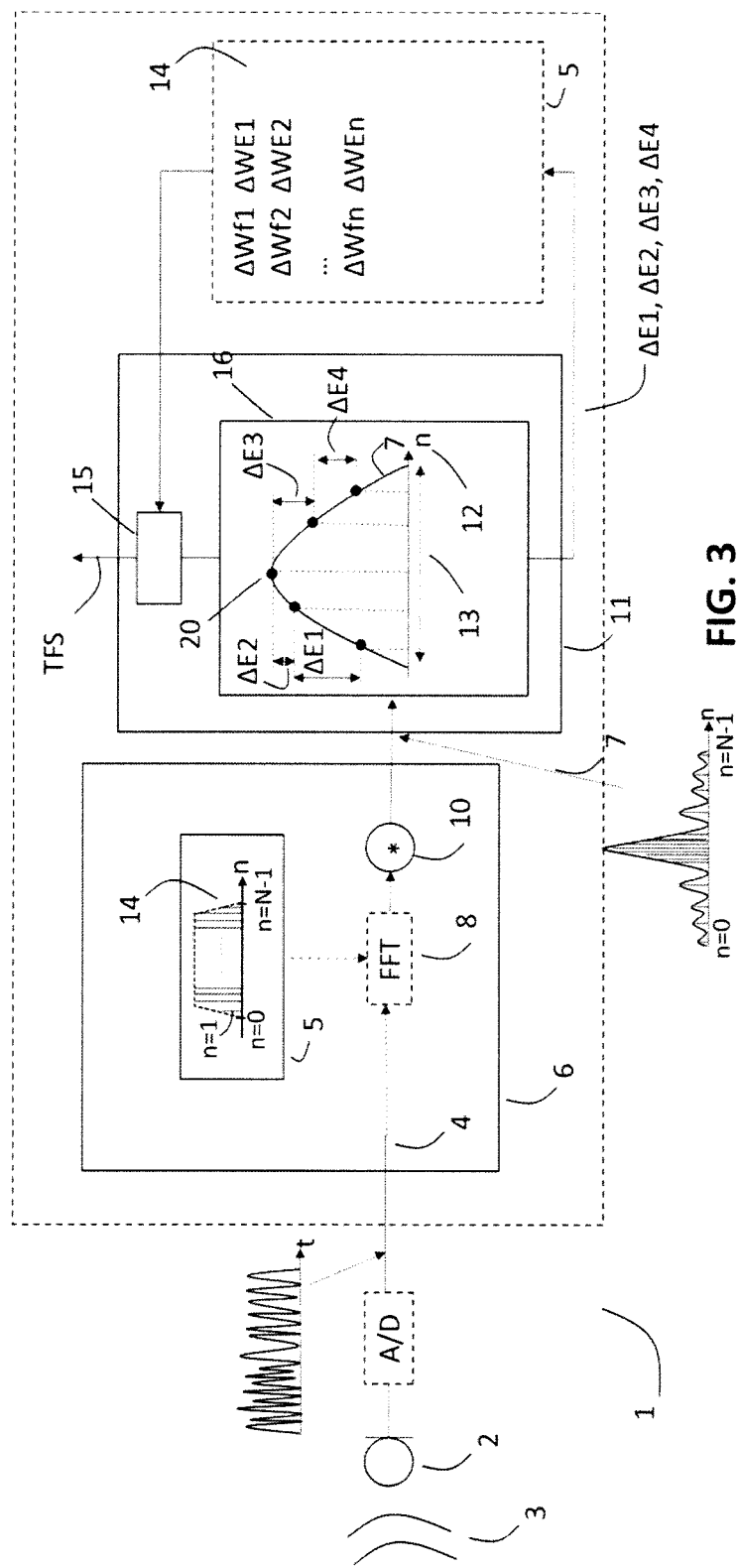
FIG. 3, illustrates another example of the cochlear stimulation system.

FIG. 3 illustrates yet a further example of the cochlear stimulation system 1 where the window analyzer 6 is configured to perform a time-to-frequency transformation 8 of the window function 14 and/or the sampled audio signal 6 and then do a convolution of the window function 14 in frequency domain and the sampled audio signal 6 in frequency domain. For example, the time-to-frequency transformation of the window function is only needed to be done for the first sample frame including the sampled audio signal 4 and not for the subsequent sample frames including another sampled audio signal 4A.

Figure 4A:
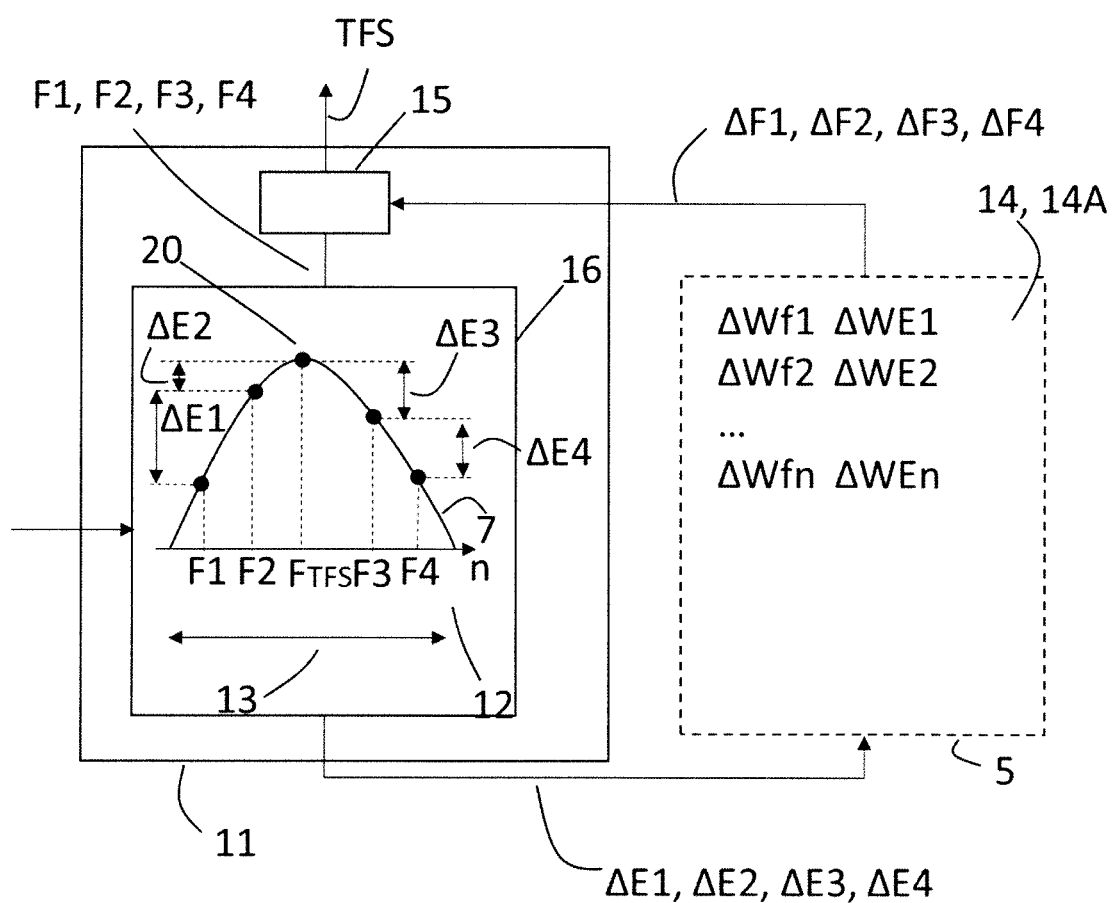
FIGS. 4A, 4B and 4C, illustrate an example of a signal processor.
Figure 4B:
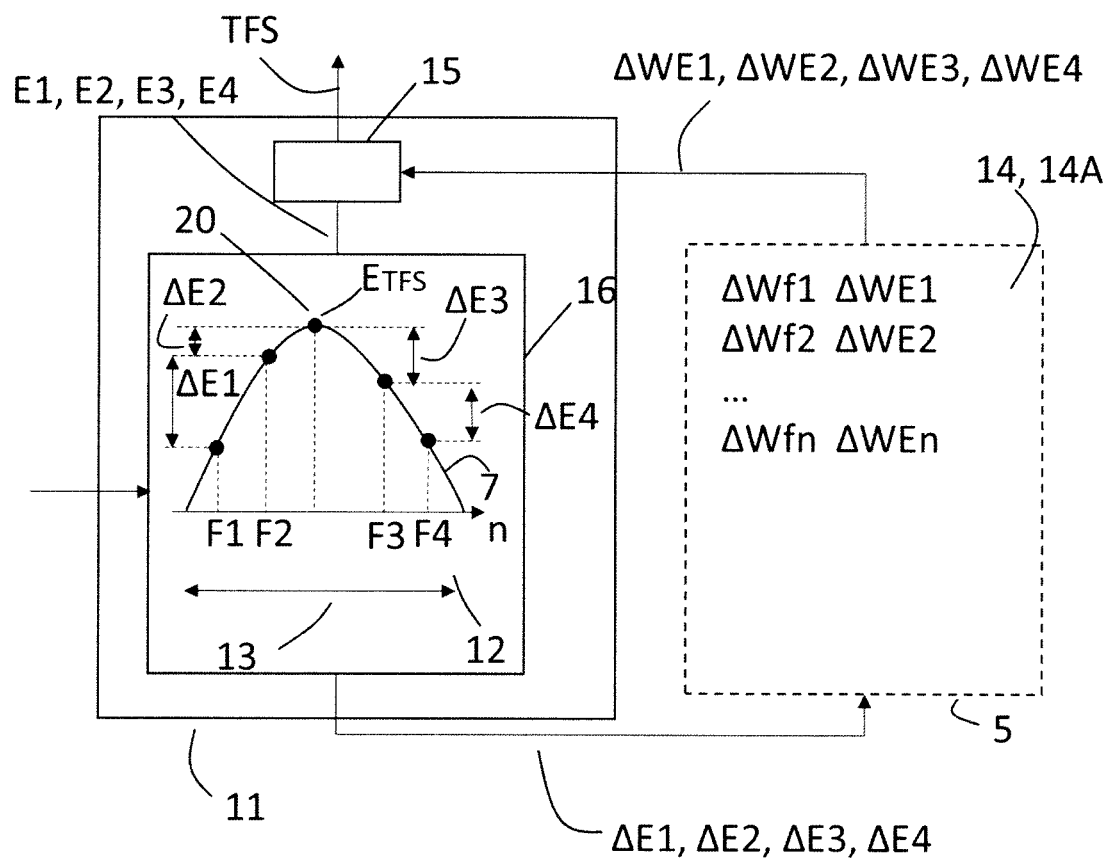
Figure 4C:
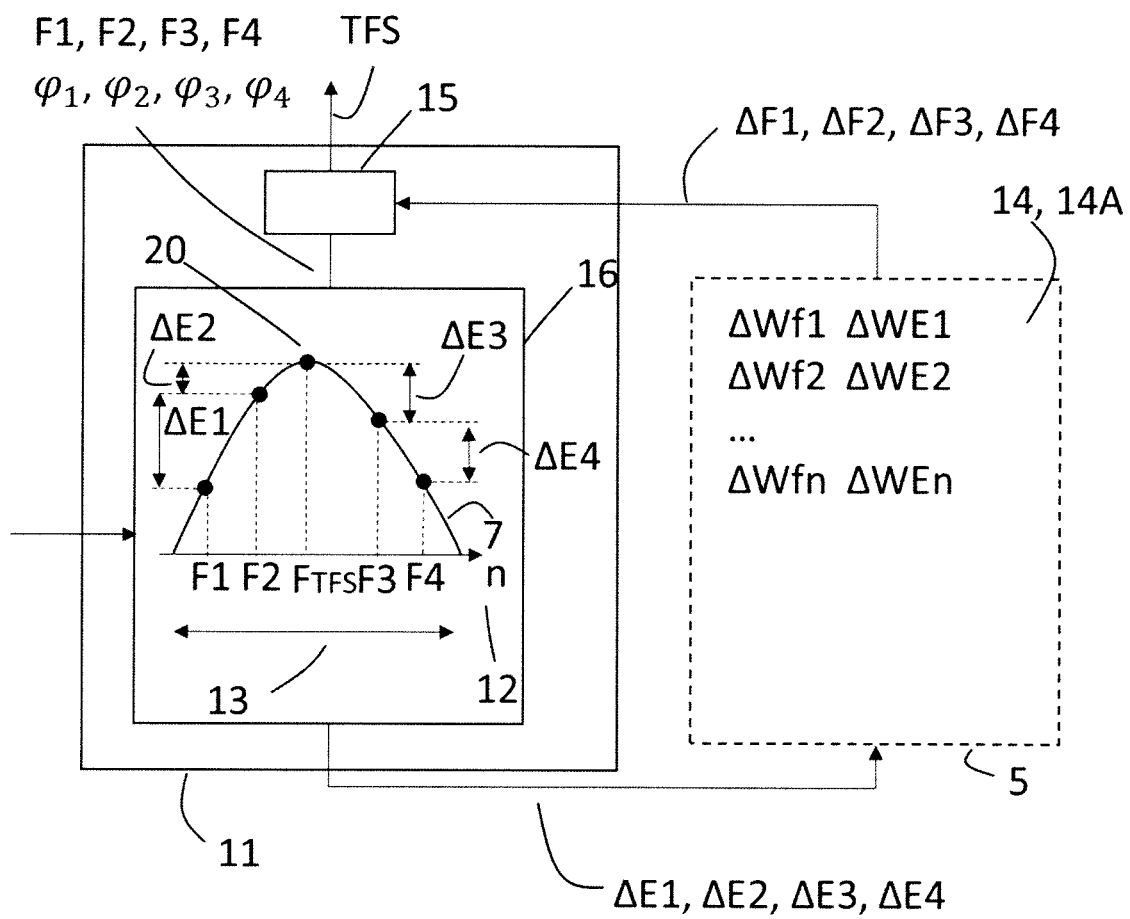

FIGS. 4A, 4B and 4C illustrate an example of the signal processor 11. In FIG. 4A, the signal processor 11 forwards the energy level difference ($\Delta E1$, $\Delta E2$, $\Delta E3$, $\Delta E4$) for the spectrum samples of the group of spectrum samples 12 to the storing unit which then estimates a frequency difference ($\Delta F1$, $\Delta F2$, $\Delta F3$, $\Delta F4$) for each of the energy level difference ($\Delta E1$, $\Delta E2$, $\Delta E3$, $\Delta E4$) based on the window function 14. The storing unit retrieves the frequency difference by correlating an energy level difference ($\Delta E1$, $\Delta E2$, $\Delta E3$, $\Delta E4$) with the stored window energy level differences ($\Delta WE1$, $\Delta WE2$, $\Delta WE3$, $\Delta WE4$) as a function of frequency, and the frequency difference of the window energy level difference which correlates best with the energy level difference is transmitted to the signal processor (15). In another example the signal processor 11 may estimate the frequency differences ($\Delta F1$, $\Delta F2$, $\Delta F3$, $\Delta F4$) by receiving the window function 14 from the storing unit based on the input to the storing unit from the signal processor, e.g. the energy level differences ($\Delta E1$, $\Delta E2$, $\Delta E3$, $\Delta E4$).

Figure 5A:
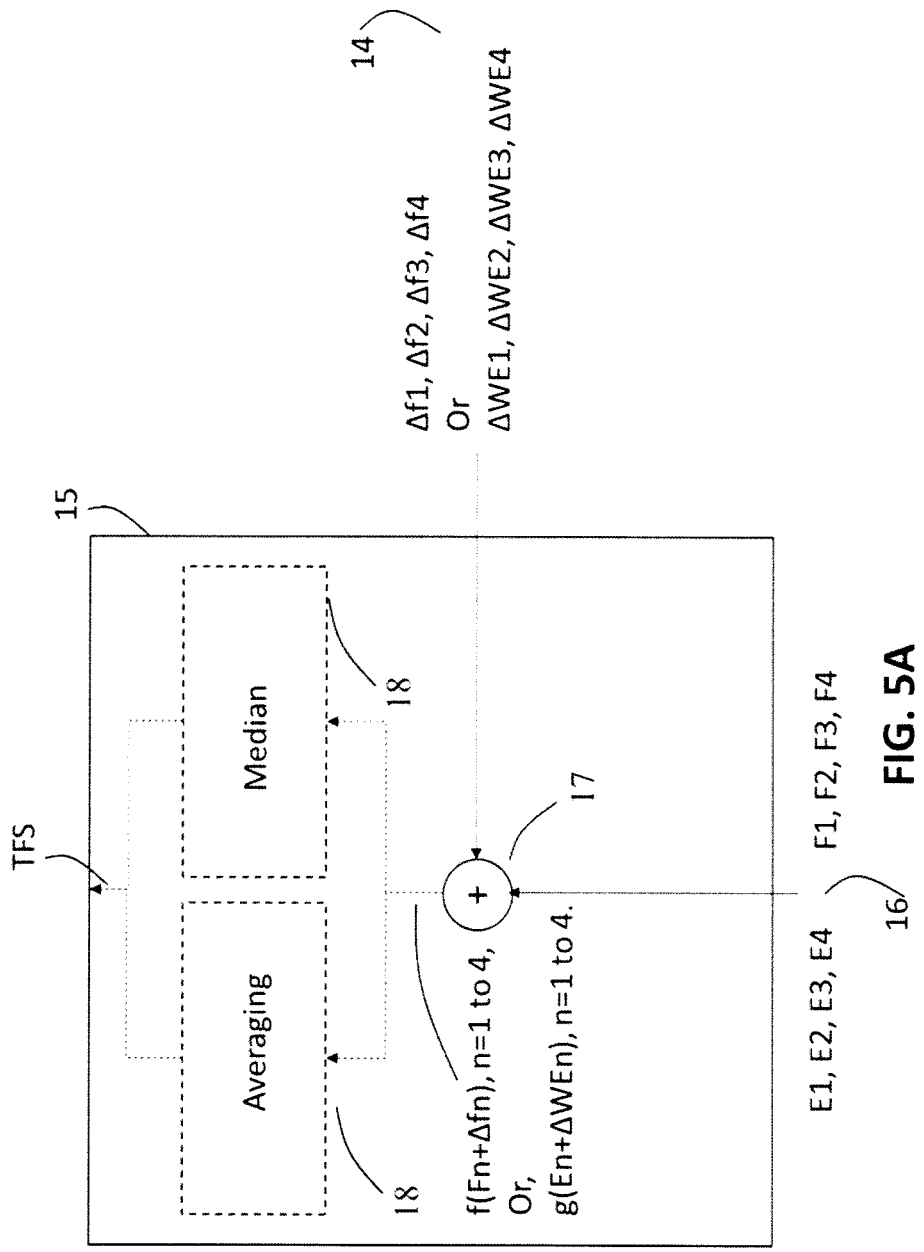
FIGS. 5A and 5B illustrate an example on how to determine the Temporal Fine Structure parameter.

The signal processor 11 is then configured to determine 15 the Temporal Fine Structure parameter TFS, including a frequency parameter $F_{TFS}$ based on the frequency differences ($\Delta F1$, $\Delta F2$, $\Delta F3$, $\Delta F4$) and the frequencies (F1, F2, F3, F4) of each of the spectrum samples of the group of spectrum samples. In the example shown in FIG. 4A, the frequency parameter $F_{TFS}$ is the frequency of the peak of the group of spectrum samples 12. In other examples, the frequency parameter $F_{TFS}$ may be different from the peak of the group of spectrum samples 12. A further explanation of how the frequency parameter is determined is illustrated in FIG. 5A.

In FIG. 4B, the signal processor 11 is further configured to determine 15 the Temporal Fine Structure parameter TFS including an Energy parameter $E_{TFS}$. The signal processor 11 transmits the energy level differences ($\Delta E1$, $\Delta E2$, $\Delta E3$, $\Delta E4$) to the storing unit which then transfer either the window function 14 or the window energy level differences ($\Delta WE1$, $\Delta WE2$, $\Delta WE3$, $\Delta WE4$) to the signal processor 11 based on the energy level differences ($\Delta E1$, $\Delta E2$, $\Delta E3$, $\Delta E4$). The window function 14 or the window energy level differences ($\Delta WE1$, $\Delta WE2$, $\Delta WE3$, $\Delta WE4$) as a function of frequency to be selected and transferred are those which either has the highest correlation factor or those which has the lowest standard deviation in relation to the energy level differences as a function of frequency. That means, that a window energy level differences which correlates best to one of the energy level differences would be selected and transferred. This will be repeated for all energy level differences transferred to the storing unit. The signal processor is then configured to determine the energy parameter Errs based on the window energy level differences ($\Delta WE1$, $\Delta WE2$, $\Delta WE3$, $\Delta WE4$) and the energy levels (E1, E2, E3, E4) of the group of spectrum samples 12. The energy parameter is interpolated based on the window energy level differences ($\Delta WE1$, $\Delta WE2$, $\Delta WE3$, $\Delta WE4$) as a function of frequency and the energy levels (E1, E2, E3, E4) as a function of frequency. In another example, the signal processor 11 is configured to estimate the window energy level differences ($\Delta WE1$, $\Delta WE2$, $\Delta WE3$, $\Delta WE4$) based on the window function 14 received from the storing unit 5. The window function to be transferred from the storing unit is the one which is most suitable for the sampled audio signal, which means that the shape of the selected window function is the one which correlates best with the shape of the sampled audio signal. Then, for each of the energy levels (E1, E2, E3, E4) as a function of frequency a window energy level difference is determined based on the window function 14.

In FIG. 4C, the signal processor 11 is configured to estimate the Temporal Fine Structure parameter TFS including a phase parameter $\varphi_{TFS}$. When the signal processor 11 has estimated the frequency parameter ($F_{TFS}$) as described in FIG. 4A, the phase parameter $\varphi$ TFS can be estimated at the frequency parameter ($F_{TFS}$) by interpolation of phases ($\varphi_1$, $\varphi_2$, $\varphi_3$, $\varphi_4$) of the spectrum samples of the group of spectrum samples (12).

Each of the spectrum sample 7 is defined by a frequency F, an energy level E and a phase $\varphi$.

In another example, the signal processor 11 may determine the phase parameter $\varphi_{TFS}$ by determine an median of the phases ($\varphi_1$, $\varphi_2$, $\varphi_3$, $\varphi_4$) of the spectrum samples of the group of spectrum samples 12.

Figure 5B:
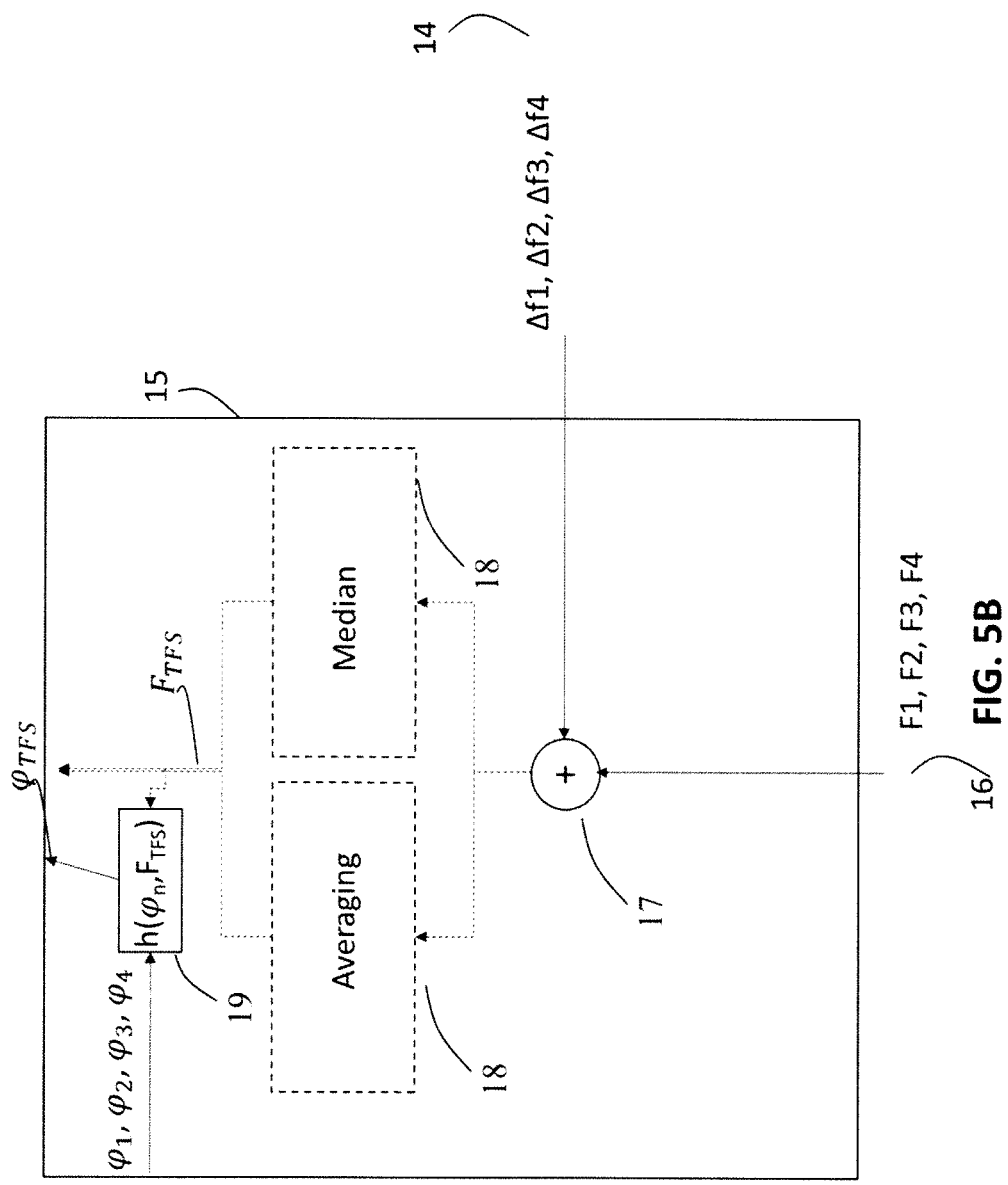

FIGS. 5A and 5B illustrate how the Temporal Fine Structure parameter TFS is determined 15. In FIG. 5A, a center frequency of a main lobe of the spectrum samples 7 for each of the spectrum samples of the group of spectrum samples 12 is determined by summing 17 the frequency differences ($\Delta F1$, $\Delta F2$, $\Delta F3$, $\Delta F4$) with the respective frequencies (F1, F2, F3, F4) for each of the spectrum samples of the group of spectrum samples 12. The frequency parameter $F_{TFS}$ is then determined by averaging 18 the calculated center frequencies (Fc1, Fc2, Fc3, Fc4) or finding the median 18 of the calculated center frequencies. For example, if considering FIGS. 4A to 4C, then following center frequencies (Fc1, Fc2, Fc3, Fc4) can be determined:

$$Fc1 = F1 + \Delta F1 + \Delta F2,$$

$$Fc2 = F2 + \Delta F2,$$

$$Fc3 = F3 + \Delta F3,$$

$$Fc4 = F4 + \Delta F3 + \Delta F4,$$

and the frequency parameter may be determined by averaging the determined center frequencies:

$$F_{TFS} = \frac{1}{4}[Fc1 + Fc2 + Fc3 + Fc4].$$

The method is not restricted to either averaging or median, the method may use interpolation 18 or any other suitable methods instead of the averaging or the median approach.

In FIG. 5A, a peak energy level of a main lobe of the spectrum samples 7 is determined for each of the spectrum samples of the group of spectrum samples 12 by summing 17 the window energy level differences ($\Delta WE1$, $\Delta WE2$, $\Delta WE3$, $\Delta WE4$) with the respective energy levels (E1, E2, E3, E4) for each of the spectrum samples of the group of spectrum samples 12. The energy parameter $E_{TFS}$ is then determined by either averaging 18 the peak energy levels or finding the median 18 of the peak energy levels. Once again, the method is not restricted to either averaging 18, or median 18, the method may use interpolation 18 or any other suitable methods instead of the averaging or the median approach. The energy parameter Errs is then determined by averaging 18 the calculated peak energy levels (Ep1, Ep2, Ep3, Ep4) or finding the median 18 of the calculated peak energy levels. For example, if considering FIGS. 4A to 4C, then following peak energy levels (Ep1, Ep2, Ep3, Ep4) can be determined:

$$Ep1 = E1 + \Delta WE1 + \Delta WE2,$$

$$Ep2 = E2 + \Delta WE2,$$

$$Ep3 = E3 + \Delta WE3,$$

$$Ep4 = E4 + \Delta WE3 + \Delta WE4,$$

and the energy parameter $E_{TFS}$ may be determined by averaging the determined energy peak levels:

$$E_{TFS} = \tfrac{1}{4}[Ep1 + Ep2 + Ep3 + Ep4].$$

In FIG. 5C, the signal processor 11 is further configured to estimate 15 the phase parameter $\varphi_{TFS}$ after the frequency parameter $F_{TFS}$ is determined 15. The phase parameter $\varphi_{TFS}$ is then estimated 19 at the frequency parameter ($F_{TFS}$) by interpolation of phases ($\varphi_1$, $\varphi_2$, $\varphi_3$, $\varphi_4$) of the spectrum samples of the group of spectrum samples (12). The estimation of the phase parameter $\varphi_{TFS}$ is not restricted to interpolation or any other suitable methods which may be used instead.

Figure 6A:
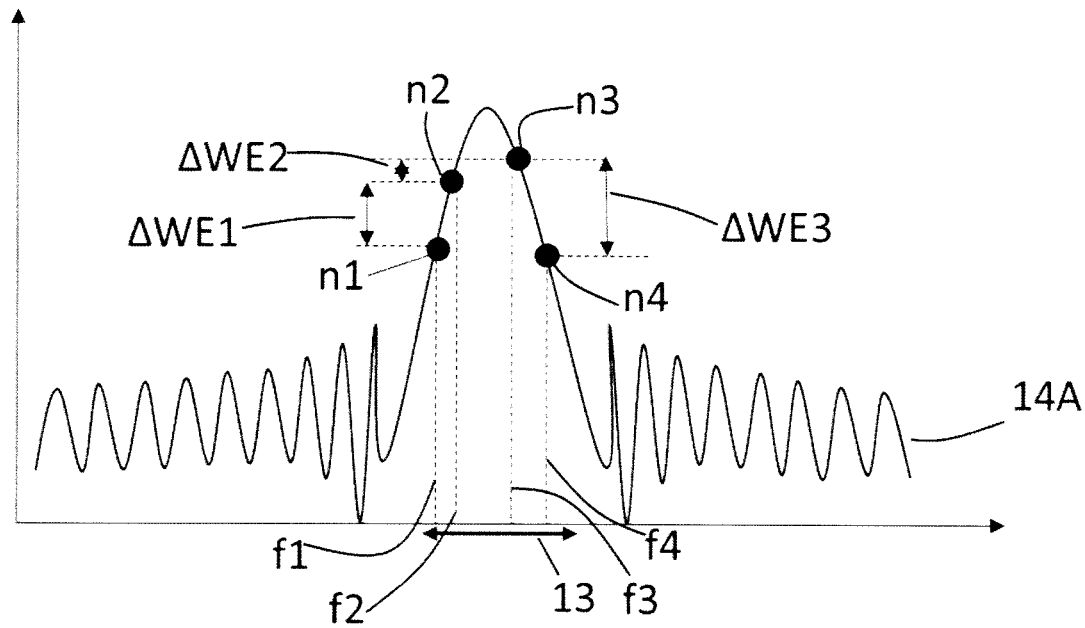
FIGS. 6A and 6B illustrate an example on how to determine the plurality of window energy level differences.
Figure 6B:
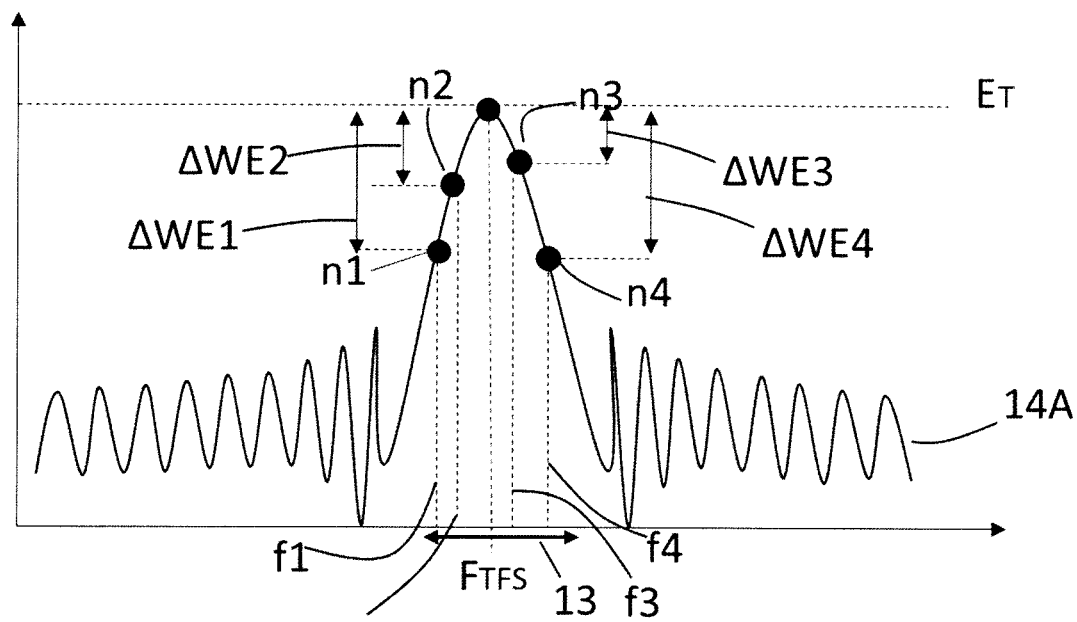

FIGS. 6A and 6B illustrates how the window energy level difference ΔWE is defined based on the window function 14. In FIG. 6A, the window energy level difference ΔWE of the plurality of window energy level difference is between a first energy level E1 of a first sample n1 at a first frequency F1 of the window spectrum 14A and a second energy level E2 at a second frequency F2 of a second sample n2, wherein the first frequency F1 and the second frequency F2 are within the range 13 of frequencies centered around the main spectrum sample.

In FIG. 6B, the window energy level difference ΔWE of the plurality of window energy level difference is between a first energy level E1 of the first sample n1 and the energy level $E_T$ at the frequency parameter $F_{TFS}$, wherein the first frequency E1 is within the range 13 of frequencies centered around the main spectrum sample 20.

FIGS. 7A, 7B and 7C illustrate three different examples of the window function 14. In FIG. 7A the input is the energy level difference ΔE determined by the signal processor 11 based on the group of spectrum samples 12, and the output is the window energy level difference ΔWE. In FIG. 7B, the input is the estimated 14 frequency difference ΔF, and the output is the window energy level difference ΔWE. In FIG. 7C, the input is the energy level difference ΔE determined by the signal processor 11 based on the group of spectrum samples 12, and the output is the frequency difference ΔF.

It is seen that the window function 14 shown in FIG. 7A is a combination of the window function 14 in FIGS. 7B and 7C.

The window function (14, W,wf) in FIG. 7A may be denoted as:

$$\Delta WE = wf(\Delta E).$$

The window function (14, W,wg) in FIG. 7B may be denoted as:

$$\Delta WE = wg(\Delta F).$$

The window function (14, W,wh) in FIG. 7A may be denoted as:

$$\Delta F = wh(\Delta E).$$

The window function illustrated in FIG. 7A may be derived as following:

$$\Delta WE = wg(wh(\Delta E).), \text{ where } wg(wh) \text{ is } wf \text{ results in}$$
$$\Delta WE = wf(\Delta E).$$

Therefore, the storing unit 5 may comprise multiple window functions 14, and the storing unit 5 or the signal processor 11 may be configured to combine two or more window functions 14 to create a new window function 14.

Figure 8A:
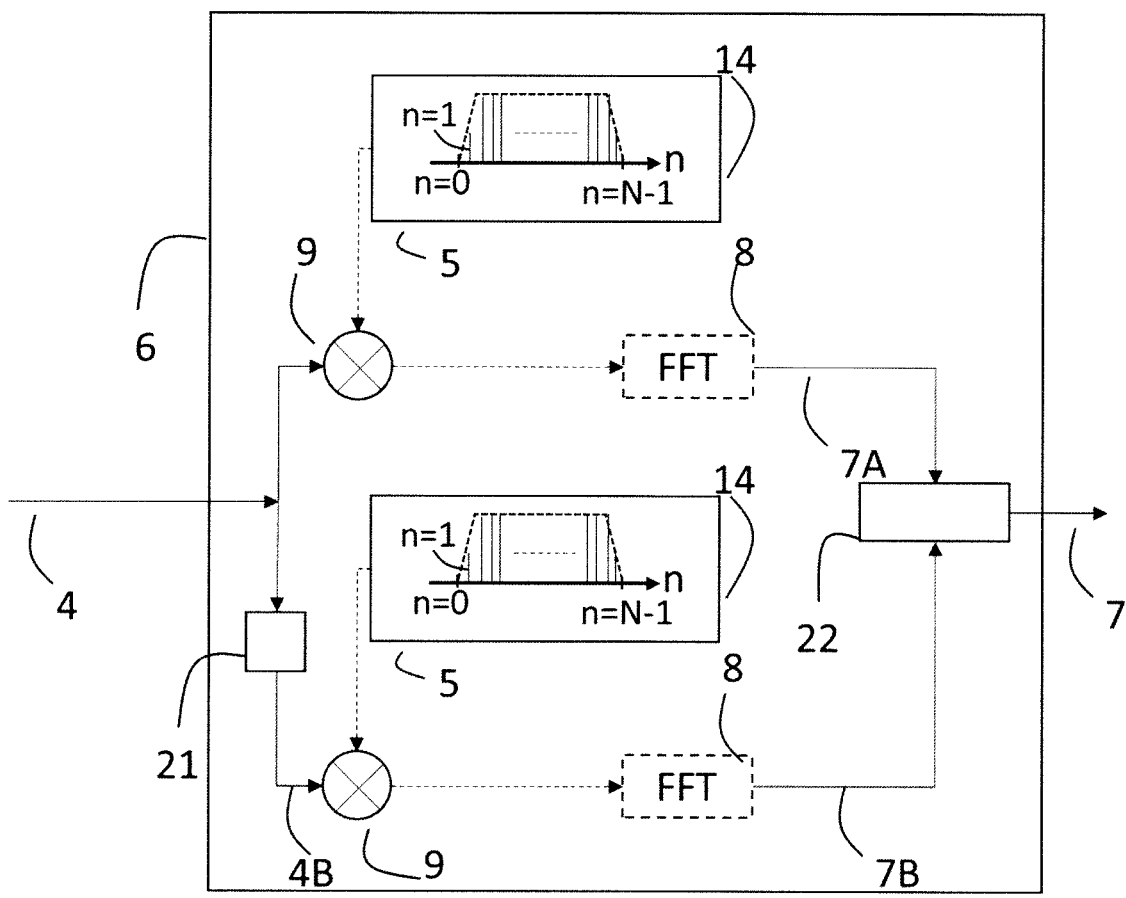
FIGS. 8A and 8B illustrates an example of a window analyzer.
Figure 8B:
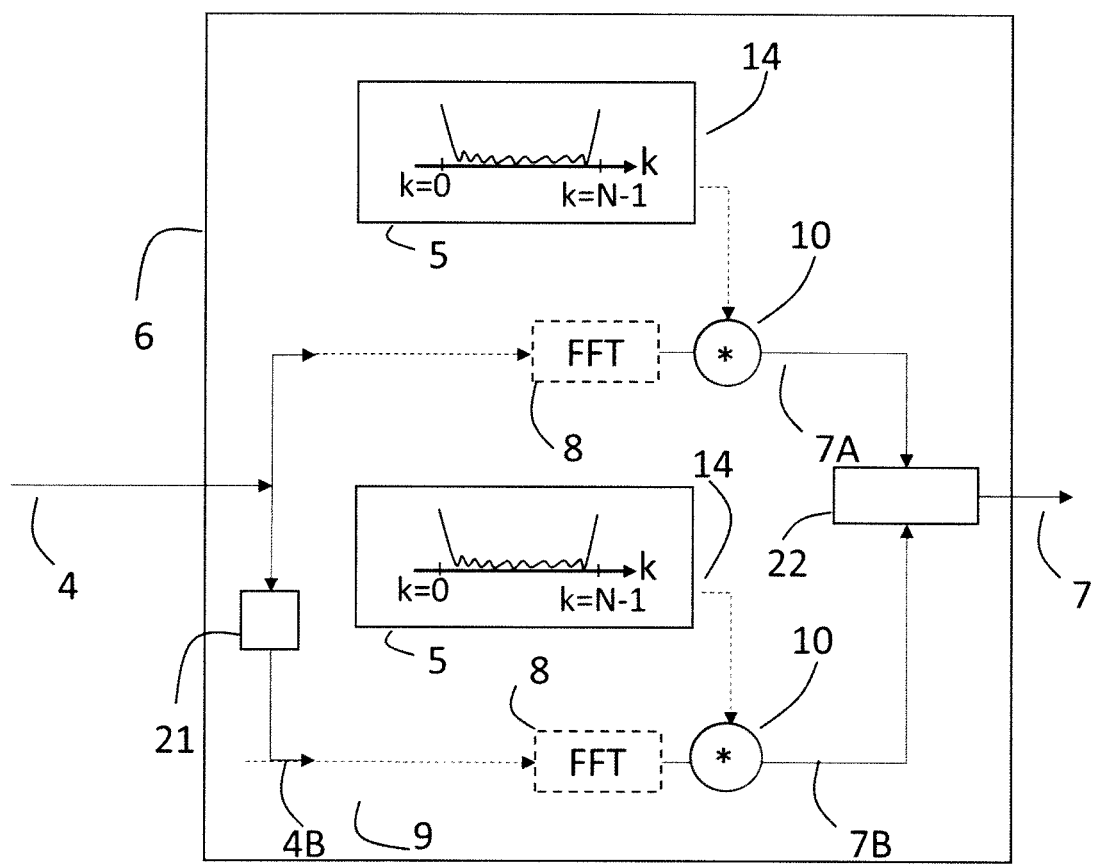

FIGS. 8A and 8B illustrate two examples on the window analyzer 6. In FIG. 8A another plurality of spectrum samples 7B is determined by applying a frequency shift 21 to the sampled audio signal 4 by multiplying the sampled audio signal 4 with a frequency shift coefficient $C_{FS}$, wherein the frequency shifted sampled audio signal 4B is multiplied 9 with the window function 14 and then transformed from time-to frequency 8. In FIG. 8B, the another plurality of spectrum samples 7B is determined by a convolution of the window spectrum 14A in frequency domain and the frequency shifted sampled audio signal 4B in frequency domain. In both FIGS. 8A and 8B, the another plurality of spectrum samples 7B is applied or combined 22 with the plurality of spectrum samples (7, 7A).

The frequency coefficient $C_{FS}$ may be defined as following:

$$C_{FS} = e^{\frac{j2\pi f_{shift}}{f_{sample}}},$$

where, $f_{shift}$ is the wanted frequency shift, and $f_{sample}$ is the present sample frequency of the sampled audio signal 4.

Figure 9:
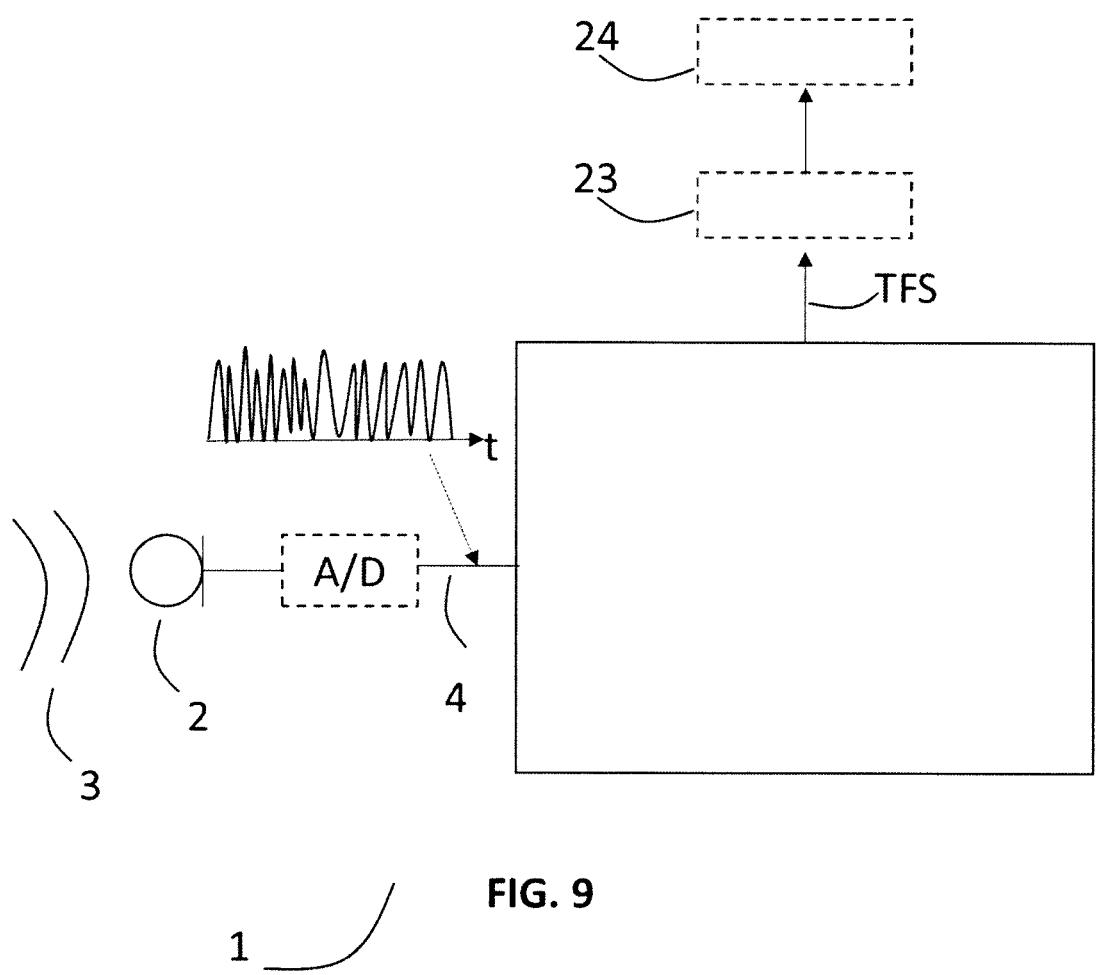
FIG. 9 illustrates an example of the cochlear stimulation system.

FIG. 9 illustrates another example of the cochlear stimulation system 1 comprising an event generator 23 configured to provide an event for providing the Temporal Fine Structure parameter TFS to an electrode of a plurality of electrodes 24, wherein the event is generated based on the phase parameter $\varphi_{TFS}$. The event is provided when a phase difference between a constant phase factor ($\varphi_0$), being between 0 and 2*pi, and the phase parameter ($\varphi_{TFS}$) is equal to zero or a predetermined constant.

Figure 10:
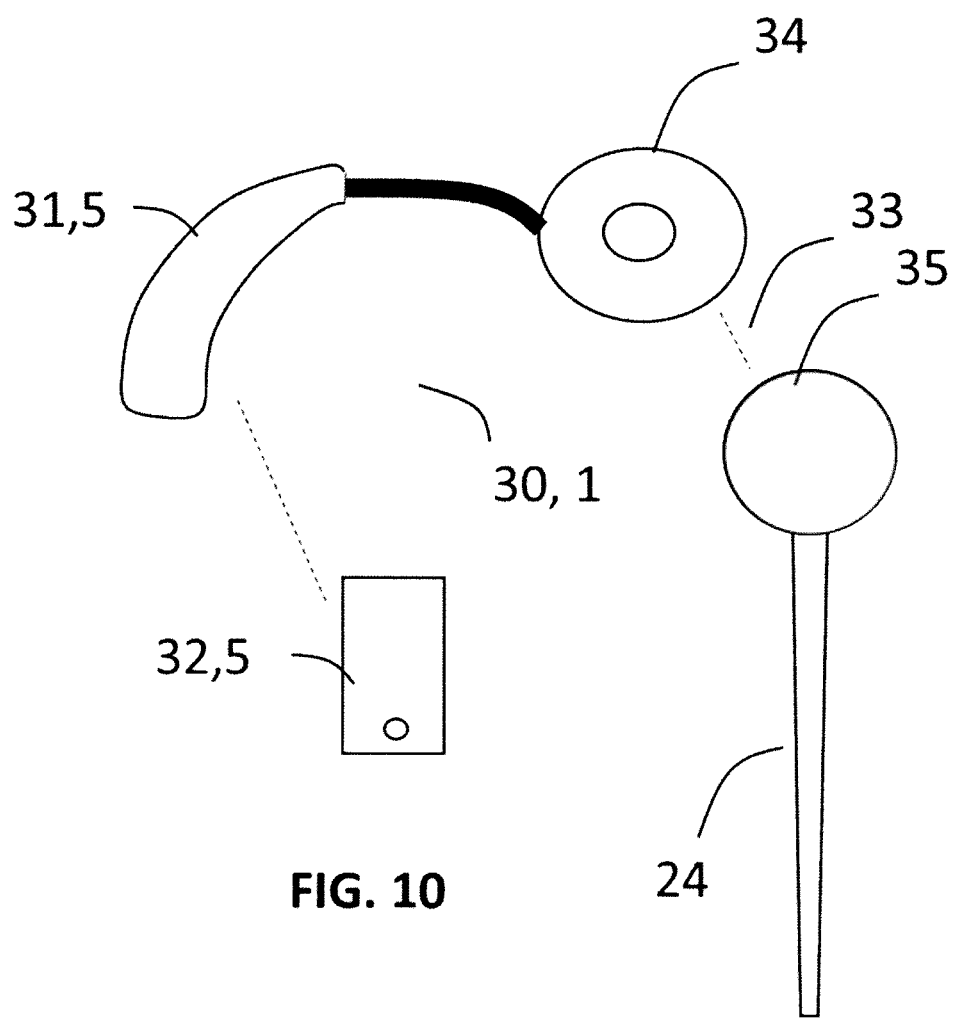
FIG. 10 illustrates an example of a cochlear implant.

FIG. 10 illustrate a cochlear implant 30 including the cochlear stimulation system 1, comprising a behind-the-ear unit 31, which may include at least a part of the cochlear stimulation system 1, e.g. the transducer 2, the window analyzer 6 and the signal processor 11, and optionally the storing unit 5. Alternatively, the storing unit 5 may be part of a mobile phone 32 or any mobile devices 32. The inductor unit 34 is connected to the behind-the-ear unit 31 via a coupling unit, such as a tube including one or more wires. The inductor unit 34 is further inductively connected to an implant unit 35. The implant unit 35 is then connected to the plurality of electrodes 24.

The invention claimed is:

1. A cochlear stimulation system for determining a Temporal Fine Structure parameter of a spectral component of the full frequency range of a sampled audio signal, the system comprising:
   a transducer configured for receiving an incoming acoustic signal, and wherein a sampled audio signal of length N samples is provided based on the incoming acoustic signal,
   an electrode array including a plurality of electrodes,
   a storing unit including a plurality of window frequency differences and a plurality of window energy level differences generated based on a window spectrum of an N length window function, and
   a window analyzer for providing a plurality of spectrum samples, where the plurality of spectrum samples are provided
      by performing a multiplication of the sampled audio signal with the window function in time domain, and performing a time to frequency transformation of the multiplied sampled audio signal, or by performing a time to frequency transformation of the sampled audio signal and the window function, and performing a convolution of the window function in frequency domain and the sampled audio signal in frequency domain, and a signal processor for estimating the Temporal Fine Structure parameter of the full frequency range of the sampled audio signal by locating a main spectrum sample having a maximum energy level of the plurality of spectrum samples provided by the window analyzer, estimating, for a group of spectrum samples of the plurality of spectrum samples, an energy level difference for one or more of the spectrum samples of the group, the energy level difference being determined between neighboring samples of the group, and wherein each of the spectrum samples of the group has a frequency within a range of frequencies centered around the main spectrum sample, estimating a frequency difference, for one or more of the energy level differences of the group of spectrum samples, based on the plurality of window frequency differences and the plurality of window energy level differences, and determining the Temporal Fine Structure parameter based on the frequency difference for one or more of the energy level difference of the group of spectrum samples, wherein each of the plurality of electrodes is configured to provide an electrical stimulation based on the Temporal Fine Structure parameter.

2. A cochlear stimulation system according to claim 1, wherein the window spectrum includes a sinusoidal signal which represents an ideal shaped sinusoidal signal of the sampled audio signal.

3. A cochlear stimulation system according to claim 2, wherein the Temporal Fine Structure parameter comprises a frequency parameter of the spectral component, and wherein the frequency parameter is determined by:

estimating a center frequency for the estimated frequency difference for one or more of the energy level differences of the group of spectrum samples, based on a frequency of one or more of the spectrum samples of the group of spectrum samples and the frequency difference of one or more of the spectrum samples of the group of spectrum samples, and computing the frequency parameter based on the center frequencies of the group of spectrum samples.

4. A cochlear stimulation system according to claim 1, wherein the Temporal Fine Structure parameter comprises a phase parameter determined at the frequency parameter by interpolation of phases of the spectrum samples of the group of spectrum samples.

5. A cochlear stimulation system according to claim 4, comprising an event generator configured to provide an event for providing the Temporal Fine Structure parameter to an electrode of the plurality of electrodes, wherein the event is generated based on the phase parameter.

6. A cochlear stimulation system according to claim 5, the event is provided when a phase difference between a constant phase factor($\varphi_0$), being between 0 and 2*pi, and the phase parameter is equal to zero or a predetermined constant.

7. A cochlear stimulation system according to claim 6, wherein the phase difference is divided by a sample frequency of a frame clock event for determining the Temporal Fine Structure parameter.

8. A cochlear stimulation system according to claim 5, wherein the event is generated after a time delay, wherein the time delay is determined by following equation;

$$\Delta t = \frac{2\pi - \varphi_{TFS}}{\Delta \varphi},$$

where $\Delta\varphi$ is a ratio between a frame clock event for determining the Temporal Fine Structure parameter and the frequency parameter, and $\varphi_{TFS}$ is the phase parameter.

9. A cochlear stimulation system according to claim 3, wherein a window energy level difference of the plurality of window energy level difference is between a first energy level of a first sample at a first frequency of the window spectrum and a second energy level at a second frequency of a second sample, wherein the first frequency and the second frequency are within the range of frequencies centered around the main spectrum sample, or and wherein a window energy level difference of the plurality of window energy level difference is between a first energy level of the first sample and the energy level at the frequency parameter, wherein the first frequency is within the range of frequencies centered around the main spectrum sample.

10. A cochlear stimulation system according to claim 3, wherein the energy level difference for one or more of the spectrum samples of the group of spectrum samples is between a first energy level of a first spectrum sample of the group of spectrum samples and a second energy level of a second spectrum sample of the group of spectrum samples.

11. A cochlear stimulation system according to claim 2, wherein the Temporal Fine Structure parameter comprises an energy parameter of the spectral component, and wherein the energy parameter is determined by:

extracting a window energy level difference of one or more spectrum samples of the group of spectrum samples based on another window function and the energy level difference of one or more of the spectrum samples of the group of spectrum samples, or based on the window function and the frequency difference for one or more of the spectrum samples of the group of spectrum samples, and determining the energy parameter based on the window energy level difference of one or more spectrum samples of the group of spectrum samples and an energy level of one or more of the spectrum samples of the group of spectrum samples.

12. A cochlear stimulation system according to claim 11, wherein the energy parameter of the spectral component is further determined by:

determining an energy compensation factor including an energy difference between an energy level of a rectangular window spectrum, at a maximum energy level of a main lobe, and an energy level of the maximum energy level of the window function, and wherein the energy parameter is combined with the energy compensation factor.

13. A cochlear stimulation system according to claim 2, wherein a window energy level difference of the plurality of window energy level differences is between a first energy level of a first sample at a first frequency of the window spectrum and a second energy level at a second frequency of a second sample, wherein the first frequency and the second frequency are within the range of frequencies centered around the main spectrum sample, or a window energy level difference of the plurality of window energy level difference is between a first energy level of the first sample and an energy level at a frequency parameter corresponding to a center frequency of main spectrum sample, wherein the first frequency is within the range of frequencies centered around the main spectrum sample.

14. A cochlear stimulation system according to claim 2, wherein the energy level difference for one or more of the spectrum samples of the group of spectrum samples is between a first energy level of a first spectrum sample of the group of spectrum samples and a second energy level of a second spectrum sample of the group of spectrum samples.

15. A cochlear stimulation system according to claim 1, wherein the energy level difference for one or more of the spectrum samples of the group of spectrum samples is between a first energy level of a first spectrum sample of the group of spectrum samples and a second energy level of a second spectrum sample of the group of spectrum samples.

16. A cochlear stimulation system according to claim 1, wherein the group of spectrum samples comprises two or more spectrum samples.

17. A cochlear stimulation system according to claim 1, wherein the window analyzer is configured to:
   determine another plurality of spectrum samples by
      applying a frequency shift to the sampled audio signal, and
      performing a multiplication of the frequency shifted sampled audio signal with the window function in the time domain and a time to frequency transformation on the multiplication, or a time to frequency transformation of the shifted sampled audio signal and a convolution of the window function in frequency domain and the frequency shifted sampled audio signal in frequency domain, and
   applying the another plurality of spectrum samples into the plurality of spectrum samples.

18. A cochlear implant comprising the cochlear stimulation system according to claim 1.

* * * * *